(12) United States Patent
Moore

(10) Patent No.: US 7,984,531 B2
(45) Date of Patent: Jul. 26, 2011

(54) RACHET HINGE FOR A KNEE OR ELBOW ORTHOSIS

(75) Inventor: Max E. Moore, Largo, FL (US)

(73) Assignee: Restorative Care of America Incorporated, St. Petersburg, FL (US)

( * ) Notice: Subject to any disclaimer, the term of this patent is extended or adjusted under 35 U.S.C. 154(b) by 1101 days.

(21) Appl. No.: 11/162,808

(22) Filed: Sep. 23, 2005

(65) Prior Publication Data
US 2007/0067957 A1    Mar. 29, 2007

(51) Int. Cl.
*E05D 11/10* (2006.01)
*A61F 5/00* (2006.01)
(52) U.S. Cl. .......................................... 16/326; 602/26
(58) Field of Classification Search ............... 16/326, 16/333–335, 343, 344; 128/878, 882; 602/5, 602/26
See application file for complete search history.

(56) References Cited

U.S. PATENT DOCUMENTS

| | | | | |
|---|---|---|---|---|
| 3,058,148 A * | 10/1962 | Von Sass et al. | 297/369 |
| 3,484,831 A * | 12/1969 | Teiji | 403/103 |
| 3,902,757 A * | 9/1975 | Yoshimura | 297/367 |
| 4,230,414 A * | 10/1980 | Cheshire | 403/95 |
| 4,252,111 A | 2/1981 | Chao et al. | |
| 4,401,344 A * | 8/1983 | Chihara et al. | 297/367 |
| 4,463,751 A * | 8/1984 | Bledsoe | 602/16 |
| 4,520,804 A | 6/1985 | DiGeorge | |
| 4,817,588 A * | 4/1989 | Bledsoe | 602/16 |
| 4,982,732 A * | 1/1991 | Morris | 602/16 |
| 5,000,169 A * | 3/1991 | Swicegood et al. | 602/16 |
| 5,169,257 A * | 12/1992 | Liou | 403/95 |
| 5,292,303 A * | 3/1994 | Bastyr et al. | 602/16 |
| 5,409,449 A * | 4/1995 | Nebolon | 602/16 |
| 5,460,599 A * | 10/1995 | Davis et al. | 602/26 |
| 5,600,876 A * | 2/1997 | Notta et al. | 29/11 |
| 5,658,241 A | 8/1997 | Deharde et al. | |
| 5,672,152 A * | 9/1997 | Mason et al. | 602/26 |
| 5,676,640 A * | 10/1997 | Biedermann | 602/26 |
| 5,814,000 A * | 9/1998 | Kilbey | 602/16 |
| 5,817,040 A * | 10/1998 | Hess et al. | 602/16 |
| 5,827,208 A * | 10/1998 | Mason et al. | 602/16 |
| 5,885,235 A * | 3/1999 | Opahle et al. | 602/16 |
| 5,921,946 A | 7/1999 | Tillinghast et al. | |
| 5,938,629 A * | 8/1999 | Bloedau | 602/16 |
| 5,954,677 A * | 9/1999 | Albrecht et al. | 602/16 |
| 5,997,493 A | 12/1999 | Young | |
| 6,004,283 A | 12/1999 | Young | |
| 6,080,122 A | 6/2000 | Gulledge | |
| 6,092,334 A * | 7/2000 | Kim | 49/8 |
| 6,203,511 B1 * | 3/2001 | Johnson et al. | 602/16 |
| 6,309,368 B1 * | 10/2001 | Herzberg et al. | 602/26 |
| 6,375,632 B1 * | 4/2002 | Albrecht et al. | 602/16 |
| 6,926,363 B2 * | 8/2005 | Yamashita | 297/366 |
| 6,993,808 B1 * | 2/2006 | Bennett et al. | 16/334 |
| 7,235,059 B2 * | 6/2007 | Mason et al. | 602/26 |
| 2004/0049291 A1 | 3/2004 | Deharde et al. | |
| 2005/0070831 A1 * | 3/2005 | Cormier et al. | 602/26 |
| 2006/0155230 A1 * | 7/2006 | Mason et al. | 602/16 |
| 2006/0206045 A1 * | 9/2006 | Townsend et al. | 602/26 |

* cited by examiner

*Primary Examiner* — Victor Batson
*Assistant Examiner* — Jeffrey O Brien

(57) ABSTRACT

A ratchet hinge for a knee or elbow orthosis having a pair of struts, connected to one strut is a pair of plates in spaced relation to one another. The other strut is pivotably connected between the plates and has a slot formed therein for receiving a locking assembly. The plates have a plurality of ratchets on their outer periphery and a locking slot formed in the edge of the plates. The locking assembly has a spring biased locking pin disposed between two plats such that the pin engages the plates to lock the hinge or allow limited movement.

8 Claims, 6 Drawing Sheets

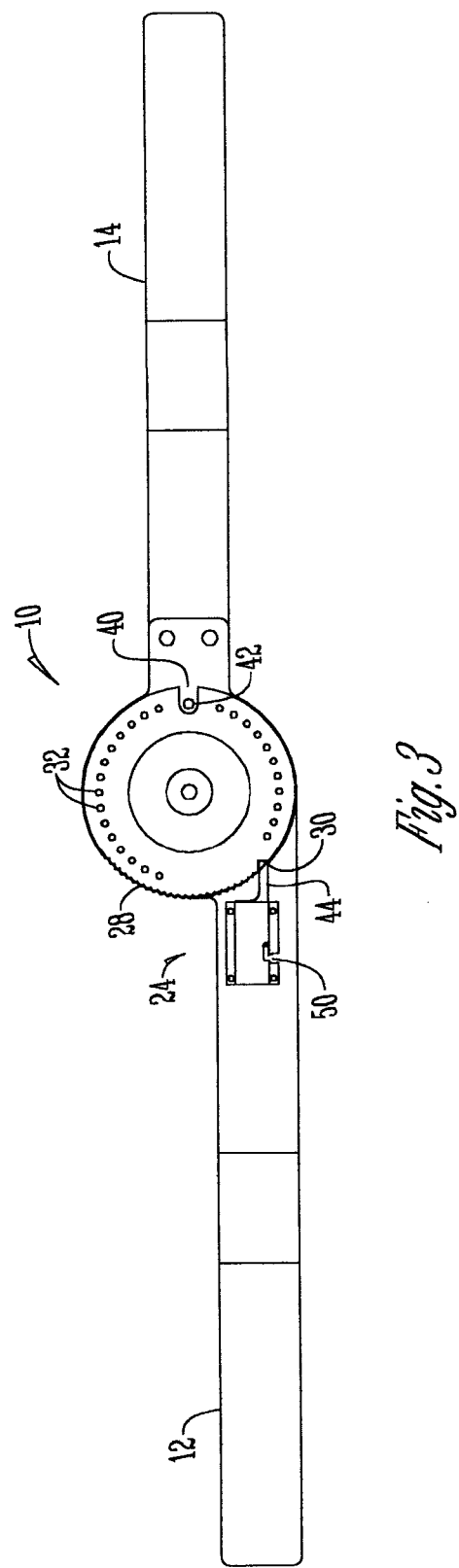

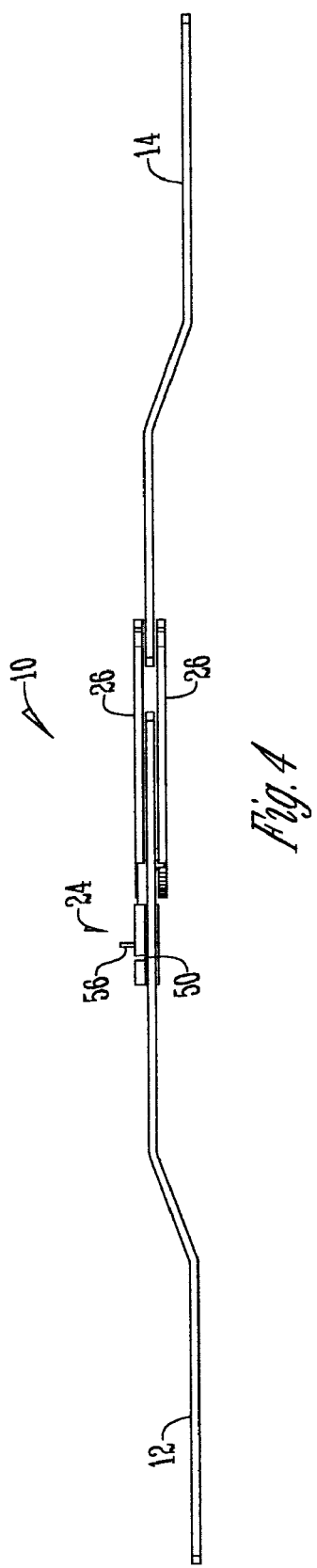

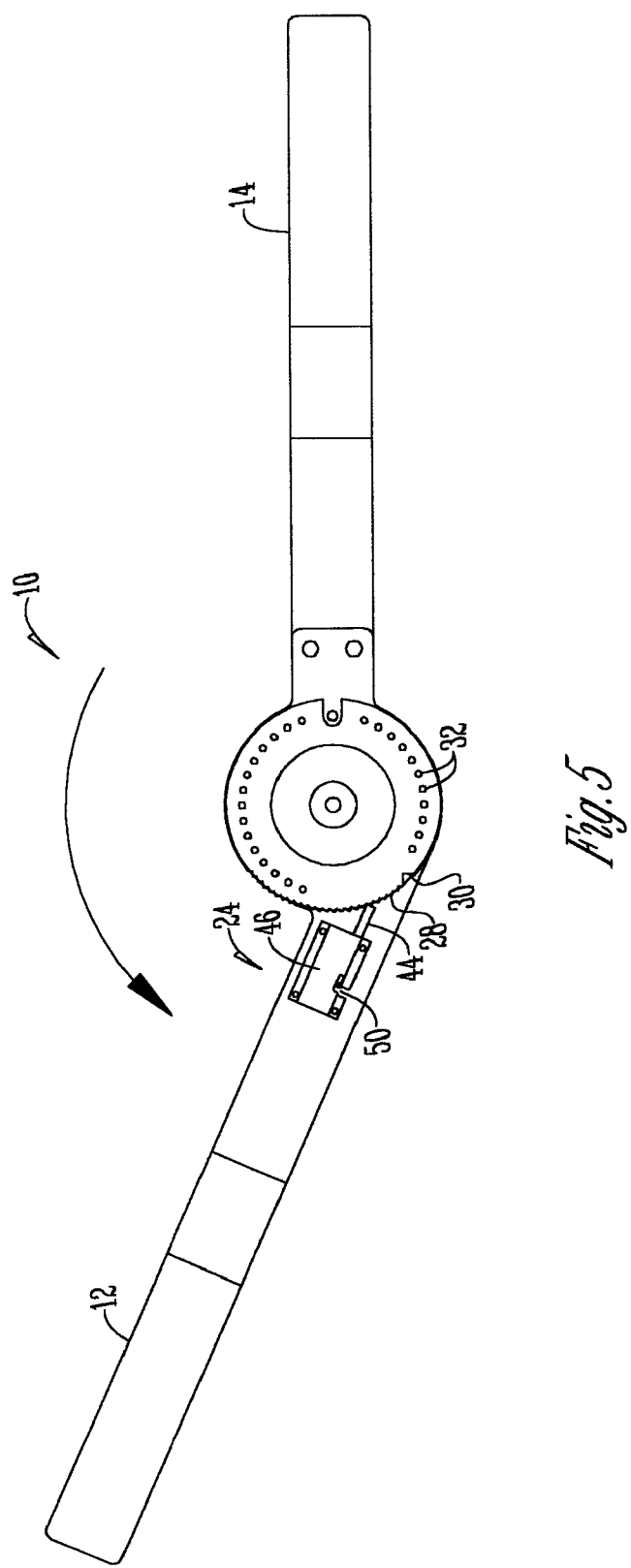

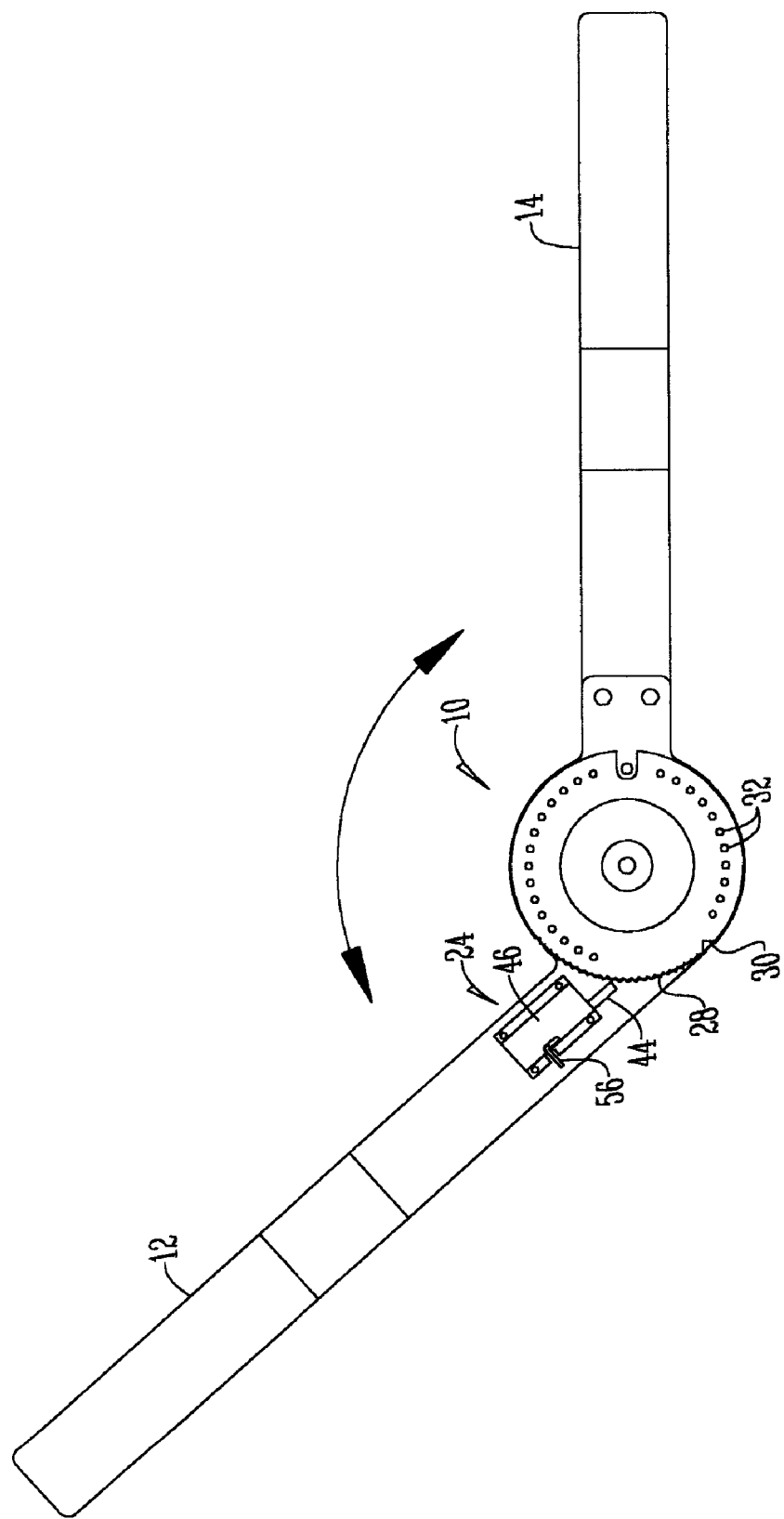

RACHET HINGE FOR A KNEE OR ELBOW ORTHOSIS

BACKGROUND OF THE INVENTION

Knee and elbow orthosis are designed for post surgery, strains, sprains, instability, ligament repairs, and soft tissue contractures, where limited range of motion or locked control of the limb is desired. Some orthosis have a hinge that connects limb brackets. Setting the hinge at incremental positions, or locking the limb in place without the use of settings or tools is desirable. Known hinges are complicated in their construction, difficult to set, and susceptible to breakage. Accordingly, a need exists for a hinge that addresses these problems.

As a result, an object of this invention is to provide a ratchet hinge that is easier to set.

A further object is to provide a ratchet hinge that is easy to assemble.

A still further object of the present invention is to provide a ratchet hinge that is of sturdy construction.

These and other objectives will be apparent based on the following written description.

SUMMARY OF THE INVENTION

A ratchet hinge for a knee or elbow orthosis having a pair of struts, connected to one strut is a pair of plates in spaced relation to one another. The other strut is pivotably connected between the plates and has a slot formed therein for receiving a locking assembly. The plates have a plurality of ratchets on their outer periphery and a locking slot formed in the edge of the plates. The locking assembly has a spring biased locking pin disposed between two plates such that the pin engages the plates to lock the hinge or allow limited movement.

BRIEF DESCRIPTION OF THE DRAWINGS

FIG. 3 is a top plan view of a ratchet hinge in a locked position;
FIG. 4 is a side elevational view of a ratchet hinge;
FIG. 5 is a top plan view of a ratchet hinge in a position providing limited movement;
and
FIG. 6 is a top plan view of a ratchet hinge in an unrestricted position.

DETAILED DESCRIPTION OF THE PREFERRED EMBODIMENT

Figure 1:
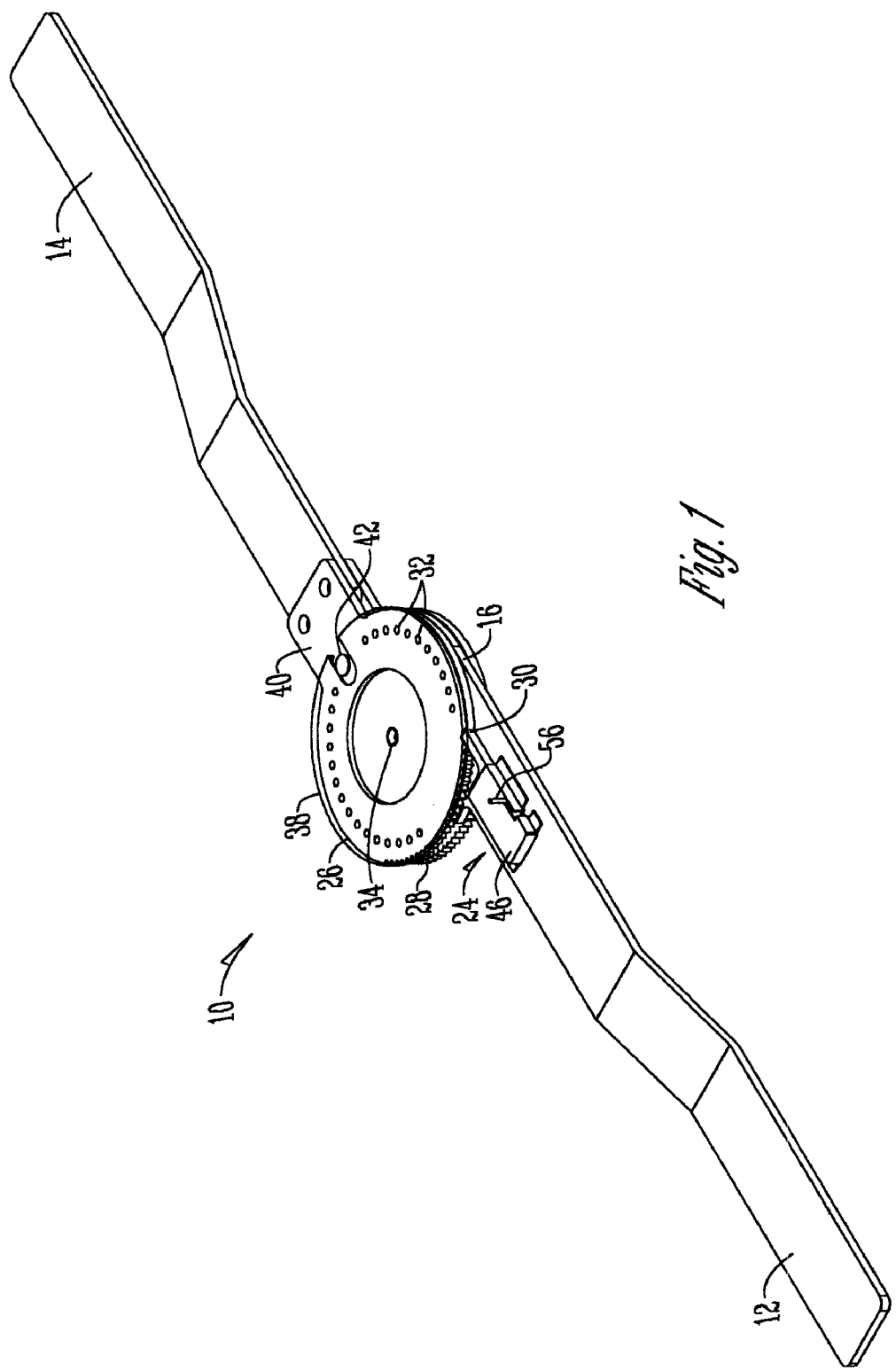
FIG. 1 is a perspective view of a ratchet hinge.
Figure 2:
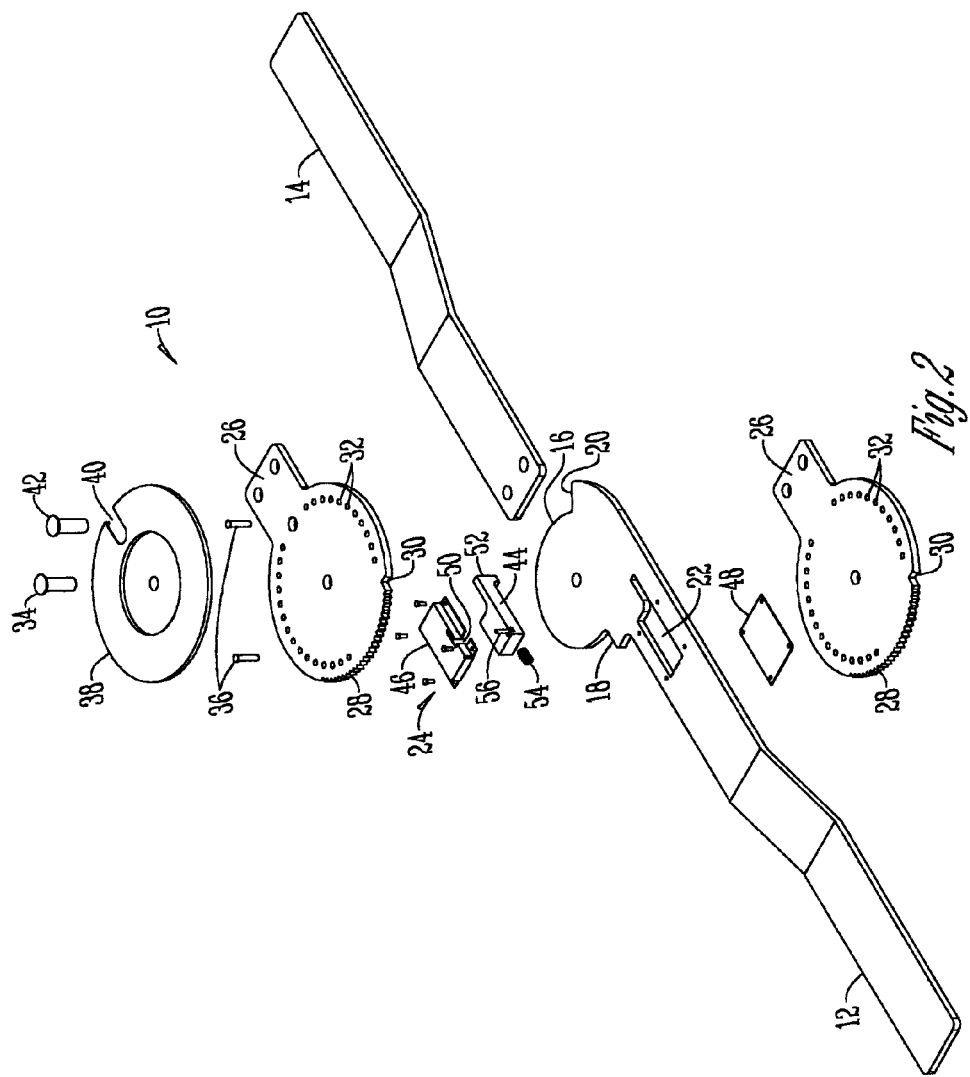
FIG. 2 is an exploded view of a ratchet hinge.

Referring to the drawings, the ratchet hinge 10 has a first strut 12 and second strut 14. The struts 12 and 14 are connected to limb brackets (not shown) at their outer ends. The first strut 12 terminates in an arcuate end 16 having a portion of its outer periphery removed to form stops 18 and 20. The first strut 12 also has a slot 22 formed therein for receiving a locking assembly 24.

The second strut 14 is connected to a pair of plates 26. The plates 26 are connected to opposite surfaces of the second strut 14 such that the plates 26 are in spaced arrangement to one another. The plates 26 have a plurality of ratchets 28 that extend around a portion of the outer periphery of the plates. At one side of the ratchets 28, a locking slot or groove 30 is formed on the outer edge of the plate 26. A plurality of stop apertures 32 are formed on an inner surface of the plates. The ratchets 28, slot 30, and apertures 32 on plates 26 are in spaced alignment.

The first strut 12 is pivotably connected between the plates 26 by a pivot pin 34 that extends through a central aperture in the plates 26 and the first strut 12.

A plurality of stop pins 36 are inserted through apertures 32 in plates 26. As the first strut 12 is rotated about pivot pin 34, the stops 18 and 20 engage stop pins 36 to limit the rotation of the first strut 12 in relation to the plates 26. A cover 38 is rotationally mounted about pivot pin 34 on top of one of the plates 26. The cover 38 has a slot 40 on its outer edge that receives a spring loaded pin 42. The spring loaded pin 42 is connected to and extends between plates 26. By depressing the spring loaded pin 42, the cover 38 may be rotated to provide access to the stop pins 36 through slot 40. In this manner, the stop pins 36 may be removed and replaced in selected apertures 32.

The locking assembly 24 that is received in slot 22 has a spring loaded locking pin 44 retained between a top plate 46 and a bottom plate 48. Plates 46 and 48 are connected to opposite surfaces of first strut 12 to cover slot 22. The top plate 46 has a retaining slot 50 through which a portion of the locking pin 44 extends.

The locking pin 44 preferably has an L-shaped end 52 that is formed to be received in locking slot 30 of plates 26. The locking pin 44 is biased toward plates 26 by a compression element 54 such as a spring or the like. To assist in retracting the locking pin 44 a handle 56 extends outwardly from pin 44 and through retaining slot 50.

In operation, the hinge 10 has three positions. One position, referred to as the locked position, is shown in FIG. 3. In this position the locking pin 44 is biased forward by the compression element 54 such that end 52 of the locking pin 44 is received in the locking slot 30. In this position, movement of the first strut 12 and second strut 14 are restricted in either direction.

A second position is shown in FIG. 5. In this position the locking pin 44 is biased forward such that end 52 engages the ratchets 28 on the outer periphery of plates 26. In this position, movement of the first strut 12 in relation to the second strut 14 is permitted in the direction of the arrow, but is restricted from movement in the opposite direction by the ratchets 28.

A third position, as shown in FIG. 6, the locking pin 44 is retracted and rotated such that the handle 56 is retained within the retaining slot 50 and end 52 of the locking pin 44 is free from engagement with either the ratchets 28 or the locking slot 30. In this position, as shown by the arrow, struts 12 and 14 are free to move in both directions in relation to one another.

What is claimed is:

1. A ratchet hinge for an orthosis comprising:
a first strut pivotably connected between a pair of plates, each plate having a plurality of ratchets on an outer periphery; and a locking slot adjacent the ratchets on the outer periphery of each plate;
a second strut connected to the plates;
a locking assembly disposed within the first strut; and
the locking assembly having a spring loaded locking pin that engages both plates to selectively position the hinge;
wherein the hinge has three positions, a locked position where the locking pin is received in the locking slot of each plate such that motion is restricted in both directions, a ratcheting position where the locking pin engages the ratchets of each plate such that motion is restricted to one direction, and a free position where the locking pin is free from engagement with the ratchets and the locking slot of each plate such that motion is unrestricted in both directions.

2. The hinge of claim 1 wherein the locking pin is disposed between a top locking pin plate and a bottom locking pin plate.

3. The hinge of claim 2 wherein the locking pin top plate has a retaining slot.

4. The hinge of claim 3 wherein the locking pin has a handle that extends outwardly and is adapted to be selectively retained with the retaining slot.

5. The hinge of claim 1 wherein when the locking pin is received within the locking slot, movement of the first and second struts is restricted in either direction.

6. The hinge of claim 1 wherein when the locking pin engages the ratchets and the first or second struts are moved in a non-restricted direction, motion terminates when the locking pin is received within the locking slot at one side of the ratchets.

7. A ratchet hinge for an orthosis comprising:
a first strut pivotably connected between a pair of plates, each plate having a plurality of ratchets on an outer periphery; and a locking slot adjacent the ratchets on the outer periphery of each plate;
a second strut connected to the plates;
a locking assembly disposed within the first strut; and
the locking assembly having a spring loaded locking pin that engages both plates to selectively position the hinge;
wherein when the locking pin engages the ratchets, movement of the first and second struts is restricted in a direction.

8. A ratchet hinge for an orthosis comprising:
a first strut pivotably connected between a pair of plates, each plate having a plurality of ratchets on an outer periphery; adjacent the ratchets a locking slot formed on an outer edge of each plate;
a second strut connected to the plates;
a locking assembly disposed within the first strut; and
the locking assembly having a spring loaded locking pin that engages the plates to selectively position the hinge;
wherein when the locking pin is free from engagement with the ratchets or the locking slot, movement of the first and second struts is unrestricted in both directions.

* * * * *